(12) United States Patent
Matson

(10) Patent No.: US 6,929,944 B2
(45) Date of Patent: Aug. 16, 2005

(54) ANALYSIS USING A DISTRIBUTED SAMPLE

(75) Inventor: Robert S. Matson, Orange, CA (US)

(73) Assignee: Beckman Coulter, Inc., Fullerton, CA (US)

(*) Notice: Subject to any disclaimer, the term of this patent is extended or adjusted under 35 U.S.C. 154(b) by 0 days.

(21) Appl. No.: 09/945,145

(22) Filed: Aug. 31, 2001

(65) Prior Publication Data

US 2003/0044799 A1 Mar. 6, 2003

(51) Int. Cl.$^7$ .......................... C12M 1/34; C12Q 1/68; C12P 19/34; A61K 38/00; C07H 1/00; C07H 21/02; C07H 21/04

(52) U.S. Cl. .................. 435/287.2; 435/6; 435/7.1; 435/91.1; 435/287.1; 530/300; 530/350; 536/23.1; 536/24.3

(58) Field of Search .................. 435/6, 91.2, 320.1, 435/283.1, 287.1, 287.2, 288.7, 7.1, 286.1, 286.5, 286.6; 530/350; 536/23.4; 436/94, 43, 50, 518, 524, 525, 527, 531; 422/62, 63, 67, 68.1, 81, 105, 112

(56) References Cited

U.S. PATENT DOCUMENTS

| | | | |
|---|---|---|---|
| 4,877,745 A | 10/1989 | Hayes et al. | 436/166 |
| 5,204,268 A | 4/1993 | Matsumoto | 436/44 |
| 5,474,796 A | 12/1995 | Brennan | 427/2.13 |
| 5,532,311 A * | 7/1996 | Sirvio et al. | 525/54.2 |
| 5,545,531 A | 8/1996 | Rava | 435/6 |
| 5,658,802 A | 8/1997 | Hayes et al. | 436/518 |
| 5,741,554 A | 4/1998 | Tisone | 427/424 |
| 6,013,789 A | 1/2000 | Rampal | 536/25.3 |
| 6,083,763 A | 7/2000 | Balch | 436/518 |
| 6,101,946 A | 8/2000 | Martinsky | 101/494 |
| 6,146,833 A | 11/2000 | Milton | 435/6 |
| 6,215,894 B1 | 4/2001 | Zeleny et al. | 382/133 |
| 6,312,960 B1 * | 11/2001 | Balch et al. | 436/518 |
| 6,485,918 B1 * | 11/2002 | Schermer et al. | 435/6 |
| 2003/0003484 A1 * | 1/2003 | Fagan | 435/6 |

FOREIGN PATENT DOCUMENTS

WO WO98/25147 6/1998 .......... G01N/33/68

OTHER PUBLICATIONS

Giles PN, Wu DJ, Foster CP, Dillon PJ and Chanock SJ (1999) Nature Biotech. 17:365–370. "Single nucleotide polymorphic discrimination by an electronic dot blot assay on semiconductor microchips."

Shuber et al (1997) Human Molecular Genetics 6:337–347. "High throughput parallel analysis of hundreds of patient samples for more than 100 mutations in multiple disease genes."

Jahn R, Schiebler W and Greengard P (1984) Proc Natl Acac Sci USA 81:1684–1687. A quantitative dot–immunobinding assay for proteins using nitrocellulose membrane filters.

Barinaga M, Science, 253:1489 (1991). Will "DNA Chip" Speed Genome Initiative?

Bains W., Bio/Technology, 10:757–758 (1992). Setting a Sequence to Sequence a Sequence.

* cited by examiner

Primary Examiner—Kenneth R. Horlick
Assistant Examiner—Frank Lu
(74) Attorney, Agent, or Firm—Hogan & Hartson, LLP

(57) ABSTRACT

The present invention is directed to the production of a sample microarray for use in detecting one or more target biopolymers in the sample. The sample microarray of this invention is formed by distributing equivalent amounts of a single sample at discrete, spatially defined locations on a substrate. Each site in the microarray, thus, has the same composition of target biopolymers. The microarray is then interrogated by one or more probes specific for one or more the target biopolymers.

71 Claims, 1 Drawing Sheet

ANALYSIS USING A DISTRIBUTED SAMPLE

FIELD OF THE INVENTION

This invention pertains to the design, fabrication, and uses of a microarray that can carry out multiplex reactions using forward blot formats for a number of applications. In particular, these applications include DNA diagnostics, genomics, genotyping, immunoassays, and proteomics.

BACKGROUND OF THE INVENTION

The analysis of unknown biopolymer targets often involve their specific binding to known biopolymer probes. The most common technique employing immobilized biopolymers is the Southern blot hybridization technique, in which a set of DNA targets is immobilized on a membrane and a solution containing labeled DNA probe molecules is used to bathe the membrane under conditions where complementary molecules will hybridize. In an analogous technique called Northern blot hybridization, RNA targets are immobilized on membranes and hybridized to complementary RNA probes. Reverse blot hybridization employs the opposite approach. Instead of immobilizing DNA targets, a set of DNA probes is immobilized on a solid surface and the unknown labeled DNA target is present in the liquid phase.

Arrays, constructed by attaching a plurality of the same or different biopolymers to discrete isolated areas on the surface of the substrate, are becoming increasingly important tools in the analysis of unknown biopolymers, such as gene expression analysis, DNA sequencing, mutation detection, polymorphism screening, linkage analysis, genotyping, and screening for alternative splice variants in gene transcripts.

Arrays of nucleic acid probes can be used to extract sequence information from, for example, nucleic acid samples. The samples are exposed to the probes under conditions that allow hybridization. The arrays are then scanned to determine to which probes the sample molecules have hybridized. One can obtain sequence information by careful probe selection and using algorithms to compare the patterns of hybridization and non-hybridization. This method is useful for sequencing nucleic acids, as well as sequence checking.

Gene expression analysis is a method of critical importance to basic molecular biological research. Since, in higher organisms, the choice of genes being expressed in any given cell has a profound effect on the nature of the cell, gene expression analysis can provide a key to the diagnosis, prognosis, and treatment of a variety of diseases in animals, including humans and plants. Additionally, gene expression analysis can be used to identify differentially expressed novel genes, to correlate a gene expression to a particular phenotype, to screen for a disease predisposition, and to conduct toxicity testing.

Typically, in the gene expression analysis, an array of probe nucleic acids is formed by attaching a set of individual gene-specific probes to a solid substrate in a regular pattern, so that the location of each probe is known. The array is contacted with a sample containing target nucleic acids under hybridization conditions. The hybrids are detected using a wide variety of methods, most commonly by employing radioactive or fluorescent labels.

Using the current reverse hybridization formats and stringency control methods, however, it remains difficult to detect low copy number (i.e., 1–100,000) nucleic acid targets, even with the most sensitive reporter groups (enzyme, fluorophores, radioisotopes, etc.) and associated detection systems (fluorometers, luminometers, photon counters, scintillation counters, etc.).

This difficulty is caused by several underlying problems associated with direct probe hybridization. One problem relates to the stringency control of hybridization reactions. Hybridization reactions are usually carried out under the stringent conditions in order to achieve hybridization specificity. Methods of stringency control involve primarily the optimization of temperature, ionic strength, and denaturants in hybridization, and subsequent washing procedures. Unfortunately, the application of these stringency conditions causes a significant decrease in the number of hybridized probe/target complexes for detection.

Another problem relates to the high complexity of DNA in most samples, particularly in human genomic DNA samples. When a sample is composed of an enormous number of sequences that are closely related to the specific target sequence, even the most unique probe sequence has a large number of partial hybridizations with non-target sequences.

A distinctive exception to the general difficulty in detecting low copy number target nucleic acid with a direct probe is the in-situ hybridization technique. This technique allows low copy number unique nucleic acid sequences to be detected in individual cells. In the in-situ format, target nucleic acid is naturally confined to the area of a cell (about 20–50 $\mu m^2$) at a relatively high local concentration. Furthermore, the probe/target hybridization signal is confined to a microscopic and morphologically distinct area. This makes it easier to distinguish a positive signal from artificial or non-specific signals than hybridization on a solid support.

Mimicking the in-situ hybridization in some aspects, new techniques are being developed for carrying out multiple sample nucleic acid hybridization analysis on micro-formatted multiplex or matrix devices, e.g., DNA chips. These chips, which are smaller than a thumbnail, contain hundreds of thousands or more of different molecular probes. These biological chips or arrays have probes arranged in arrays, each probe assigned a specific location, such as micro-wells of a chip. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location. These hybridization formats are micro-scale versions of the conventional "reverse dot blot" and "sandwich" hybridization systems.

Biological chips, or arrays, are useful in a variety of screening techniques for obtaining information about either the probes or the target molecules. For example, a library of peptides can be used as probes to screen for drugs. The peptides can be exposed to a receptor, and those probes that bind to the receptor can be identified.

The micro-formatted hybridization can also be used to carry out "sequencing by hybridization" (SBH) (see M. Barinaga, *Science*, 253:1489 (1991); W. Bains, *Bio/Technology*, 10:757–758 (1992)). SBH makes use of all possible n-nucleotide oligomers (n-mers) to identify n-mers in an unknown DNA sample, which are subsequently aligned by algorithm analysis to produce the DNA sequence.

There are two formats for carrying out SBH. One format involves creating an array of all possible n-mers on a support, which is then hybridized with the target sequence. This is a version of the reverse dot blot. Another format involves attaching the target sequence to a support, which is sequentially probed with all possible n-mers. Both formats, however, have the fundamental problems of direct probe hybridizations and additional difficulties related to multiplex hybridizations. This inability to achieve "sequencing by hybridization" by a direct hybridization method leads to a so-called "format 3," which incorporates a ligase reaction step. While providing some degree of improvement, it actually represents a different mechanism involving an enzyme reaction step to identify base differences.

Regardless of the format, all current micro-scale DNA hybridizations and SBH approaches do not overcome the underlying problems associated with nucleic acid hybridization reactions. There remains, therefore, a need for improved microarray techniques.

SUMMARY OF THE INVENTION

Figure 1:
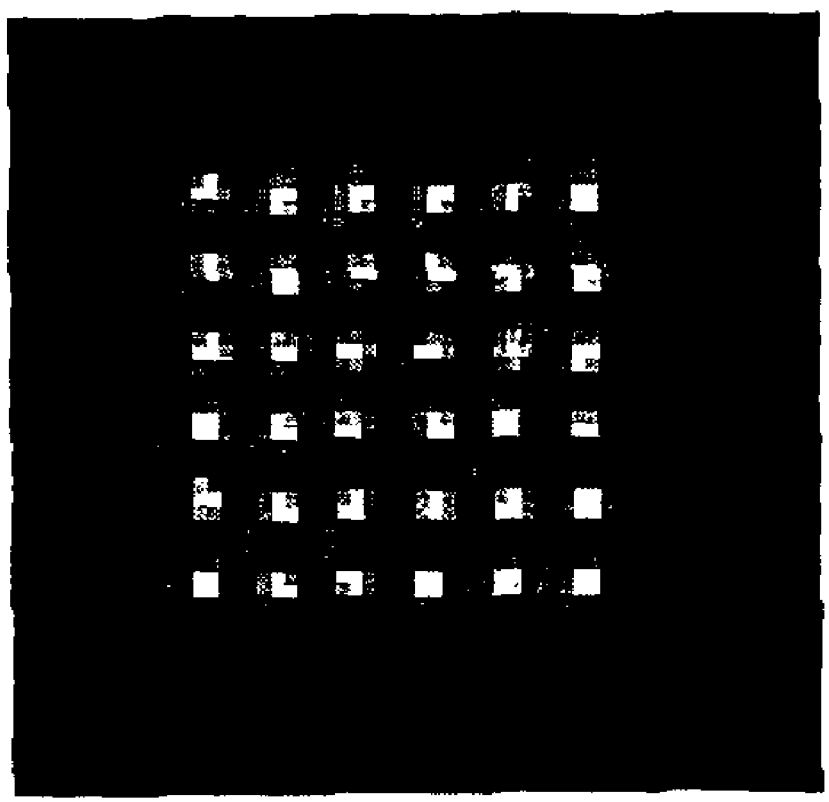
FIG. 1 illustrates a microarray containing a human IgG sample evenly distributed into 200 pL aliquots, each containing approximately 1 femtomole of protein and covalently attached onto an acryl fluoride-activated polypropylene substrate. The sample array was developed using an anti-human IgG-alkaline phosphatase conjugate and signals generated using the ELF reagent.

The present invention is directed to the production of a sample microarray for use in detecting one or more target biopolymers and/or analytes in the sample. The sample microarray of this invention is formed by distributing equivalent amounts of a single sample at discrete, spatially defined locations on a substrate. The method is capable of dispensing and assaying sample aliquots onto the microarray which may contain, for example, picomole, femtomole, attomole or zeptomole amounts of the target. Each site in the microarray, thus, has the same composition of target biopolymers and/or analytes. The microarray is then interrogated by one or more probes specific for one or more of the target biopolymers and/or analytes. This invention employs the Southern blot format in the form of a microarray of defined density that can be probed in multiplex. More specifically, one aspect of this invention provides a method for detecting one or more target biopolymers in a sample, comprising:

a) preparing a microarray of the sample by dispensing aliquots of the sample at discrete sites onto a substrate and immobilizing the biopolymers onto the substrate, wherein each of the aliquots contains equivalent amounts of the target biopolymers;

b) contacting the microarray with one or more probes under conditions that allow the formation of one or more complexes comprising a target biopolymer complexed to a probe specific for that biopolymer; and c) detecting the presence of the complexes as a measurement for the presence or the amount of the target biopolymers in the sample.

The probe may also include a reporter. The reporter may be selected from a group consisting of dyes, chemiluminescent compounds, enzymes, fluorescent compounds, metal complexes, magnetic particles, biotin, hapten, radio frequency transmitters, and radioluminescent compounds.

This invention is suitable for the detection of biopolymers including, but not limited to, nucleic acids, polypeptides, and carbohydrates. In addition, this invention is suitable for the detection of other analytes of interest, including, but not limited to, drugs and small organic molecules.

This invention provides a method of addressing a distributed target sample simultaneously with a number of different probes. The method of this invention is useful for analyzing and quantifying several targets within a single sample using a microarray comprising equivalent aliquots of the sample to which various probes are applied. For example, the present invention is well suited for use in creating polynucleotide arrays, such as gene expression microarrays for use in gene expression analysis. The sample microarrays may also be used for the evaluation or identification of biological activity. The present invention may also be used in creating polynucleotide microarrays for the purpose of polynucleotide sequencing.

DETAILED DESCRIPTION OF THE INVENTION

The present invention is directed to the production of a sample microarray for use in detecting one or more target biopolymers and/or analytes in a sample. The sample microarray of this invention is formed by distributing equivalent amounts of a single sample at discrete, spatially defined locations on a substrate, which is then interrogated by a probe specific for the target biopolymer. The method is capable of dispensing and assaying sample aliquots onto the microarray which may contain, for example, picomole ($10^{-12}$), femtomole ($10^{-15}$), attomole ($10^{-18}$), or zeptomole ($10^{-21}$) amounts of the target. The method of this invention is particularly useful in a multiplex assay environment in which a single sample array is contacted with a plurality of probes to determine whether one or more of a plurality of predetermined target biopolymers is present in a sample.

More specifically, one embodiment of this invention comprises a method for detecting a target biopolymer in a single sample, comprising:

a) preparing a microarray of the sample by dispensing aliquots of the sample at discrete sites onto a substrate and immobilizing the biopolymer onto the substrate, wherein each of the aliquots contains equivalent amounts of the target biopolymer;

b) contacting the microarray with one or more probes under conditions that allow the formation of one or more complexes comprising a target biopolymer complexed to a probe specific for that biopolymer; and c) detecting the presence of the complexes as a measurement for the presence or the amount of the target biopolymer in the sample.

This invention is suitable for the detection of biopolymers including, but not limited to, nucleic acids, polypeptides, and carbohydrates. In addition, this invention is suitable for the detection of other analytes of interest including, but not limited to, drugs, small organic molecules, carbohydrates, cells, cellular fragments, and tissues, provided that the analyte can be fixed to the support and a detection probe or reagent for the analyte is available or can be prepared.

The term "biopolymer," as used herein, includes, but is not limited to, nucleic acids, polypeptides, carbohydrates, and analogues thereof. As used herein, the terms "nucleic acid," "polynucleotide," and "oligonucleotide" refer to a polymer of two or more modified or unmodified deoxyribonucleotides or ribonucleotides, either in the form of a separate fragment or as a component of a larger construction. Examples of polynucleotides include, but are not limited to, DNA, RNA, or DNA analogs, such as PNA (peptide nucleic acid), and any chemical modifications thereof. The DNA may be a single- or double-stranded DNA, cDNA, or a DNA amplified by PCR technique. The RNA may be an mRNA. The polynucleotide may be derived synthetically or by cloning.

As used herein, "peptide" refers to a polymer of amino acids chemically bound by amide linkages (CONH). An "amino acid" is defined as an organic molecule containing both an amino group ($NH_2$) and a carboxylic acid (COOH). As used herein, the term "peptide" includes peptides, polypeptides, and proteins. A protein may comprise one or multiple polypeptides, linked together by disulfide bonds. Examples of the protein include, but are not limited to, antibodies, antigens, ligands, receptors, etc.

The term "antibody," as used herein, refers to immunoglobulins that are produced in response to the detection of a foreign substance, and includes intact molecules as well as functional fragments thereof, such as Fab, $F(ab')_2$, and Fv.

As used herein, "carbohydrate" refers to polymers of the formula $C_n(H_2O)_n$, and includes disaccharides, trisaccharides, etc., as well as macromolecular polymeric substances, such as starch, glycogen, and cellulose polysaccharides.

The method of this invention provides a novel method for the multiplex analysis of a sample using a microarray format that allows for the simultaneous interrogation of a single sample with multiple probes. Like the familiar "chip" technologies, the method of this invention interrogates immobilized biopolymers with other biopolymers. However, in contrast to conventional microarray approaches which typically employ the reverse blot format, the method, according to the present invention, follows the Southern blot format by immobilizing a single sample containing one or more biopolymers of interest as discrete aliquots or printed elements on a substrate in the form of a microarray. According to the present invention, each printed element on the sample microarray contains an equivalent amount of the target biopolymer(s) of interest. This sample microarray is then interrogated with one or more known probes.

The present invention provides many advantages over conventional multiplex analysis methods. For example, hybridization efficiency is increased relative to that of reverse blot oligonucleotide probe microarray assays, since according to the present invention, the target is randomly attached to the substrate and, thus, more accessible to the probe. In contrast, in the conventional reverse blot format, the probe is attached at a high molecular surface density which does not allow for the efficient binding of the target to the probe due to steric hindrance.

Another advantage of the method of this invention over conventional methods is that, according to this invention, a single sample can be interrogated with a plurality of probes in order to analyze the sample for the presence of multiple biopolymers and/or analytes.

Yet another advantage of the method of this invention is that it is not necessary to label the target in the sample in order to detect the target. Furthermore, the method of this invention allows for the simultaneous detection of different targets within a single aliquot on the microarray using multiple-labeled probes.

The preparation of a microarray of a single sample according to this invention comprises dispensing discrete, equivalent aliquots (also referred to in the art as "printed elements") of the sample on a substrate, followed by immobilizing the biopolymers on the surface of the substrate. The terms "microarray" and "sample microarray," as used herein, refer to a collection of aliquots ($S_1$, $S_2$, $S_3$, etc. . . . ) from a single sample (S) arranged on a substrate in a spatially defined and addressable manner. The dispensed aliquots are equivalent in composition and in the amount of target(s), that is, $S_1=S_2=S_3$, etc. Typically, the sample aliquots are dispensed on a substrate as an array of small dots or printed elements. Each dot is preferably from 1 to 500 microns in diameter and contains between about zeptomole ($10^{-21}$) to picomole ($10^{-12}$) quantities of the target biopolymer(s) and/or analyte(s) present in the sample. Accordingly, each element on the microarray of this invention contains the same composition (i.e., the same sample components at the same concentration). A typical microarray of this invention comprises a substrate that is approximately 10 mm by 10 mm and contains a grid of 20×20 printed elements (aliquots). However, it is to be understood that the arrays of this invention may include substrates that are larger or smaller than 10 mm by 10 mm, and/or may contain fewer or greater then 20×20 printed elements.

In order to prepare ordered arrays of aliquots of the single sample, such as grids or 1×n arrays of immobilized biopolymers, with each aliquot dispensed at site-specific locations, a pre-selected site on the surface of the substrate is exposed to an aliquot of the sample. For purposes of the present invention, it is not crucial which particular method is used to carry out the step of contacting the aliquots with the substrate. What is critical to the present invention is that the method is capable of dispensing an equivalent-sized aliquot to each site in the array, such that each site contains substantially the same amount of target biopolymer(s). Thus, in one embodiment, the dispensing step can be accomplished manually by applying an aliquot of biopolymer solution to a preselected location on the substrate. Alternatively, the dispensing step may be carried out by jet printing or other "drop-on-demand" devices that permit the fabrication of microarrays, as shown by Brennan (U.S. Pat. No. 5,474,796), Tisone (U.S. Pat. No. 5,741,554), and Hayes et al. (U.S. Pat. No. 5,658,802), the relevant content of which is incorporated herein by references. Other dispensing methods suitable for purposes of this invention include solid or open capillary device contact printing, microfluidic channel printing, silk screening, and printing using devices based upon electrochemical or electromagnetic forces or molecular self-assembling principals. For example, thermal inkjet printing techniques utilizing commercially available jet printers and piezoelectric microjet printing, solenoid, thermal or other non-contact dispensing techniques, such as described in U.S. Pat. No. 4,877,745, may be utilized to dispense sample aliquots onto the substrate. A Biomek High Density Replicating Tool (HDRT) (Beckman Coulter, CA) may also be used for an automatic gridding.

The aliquots are preferably deposited onto a substrate at about 1 to 1536 discrete sites per square millimeter of substrate surface area. In one embodiment, the substrate is a multiple well microplate, and the aliquots are deposited at between 1 to 1536 discrete sites per well of the microplate.

In one embodiment, the sample is combined with an internal standard, such as a heterologous dye-labeled nucleic acid or protein prior, to dispensing the sample. In this embodiment, the internal standard is also evenly distributed on the array along with the target biopolymer(s) in the sample aliquots. The internal standard allows for the determination of the target biopolymer and/or concentration in each aliquot.

Once the aliquots are dispensed onto the substrate, the target biopolymer and/or analyte (the "target") contained in each of the aliquots is immobilized onto the surface of the substrate. In one embodiment, the target is immobilized on the substrate surface by direct adsorption, as described in commonly assigned and co-pending U.S. patent application Ser. No. 09/694,701, filed Oct. 23, 2000 and entitled "Immobilization of Biopolymers to Aminated Substrates by Direct Adsorption," which is specifically incorporated herein by reference. In this embodiment, a target is immobilized on a substrate by contacting the target with the substrate under a condition sufficient for a direct adsorption of the target to the substrate. A condition is sufficient if it allows the target to become adsorbed on the surface of the substrate in a stable way. Here, the term "direct adsorption" means adsorption without any chemical linkers. In this embodiment, the target is immobilized on a substrate by simple air-drying on the substrate. The air-drying step is conducted for a period of time sufficient to allow adsorption of the target solution. The length of the air-drying time depends on the volume of the aliquots applied to the substrate, temperature, and humidity.

Alternatively, the target is immobilized on the substrate by covalent bonds, for example, according to the methods disclosed in U.S. Pat. Nos. 6,013,789 and 6,146,833, each of which is specifically incorporated herein by reference. For example, U.S. Pat. No. 6,013,789 describes the immobilization of imidazole-activated nucleic acids to amino-polypropylene supports, and U.S. Pat. No. 6,146,833 describes immobilization to acyl fluoride-activated supports.

The substrate may be made of a variety of materials. In one embodiment, the substrate is made of crosslinked polymers including, but not limited to, polypropylene, polyethylene, polystyrene, and carboxylated polyvinylidene fluoride. Polypropylene and polystyrene are organic materials that can be surface-activated, but otherwise are chemically inert under harsh chemical conditions. Polypropylene can be used in very corrosive environments. For example, polypropylene has good chemical resistance to a variety of mineral acids (e.g., hydrochloric acid), organic acids (e.g., formic acid, acetic acid), bases (e.g., ammonium hydroxide, potassium hydroxide), salts (e.g., sodium chloride), oxidizing agents (e.g., peracetic acid, iodine solutions), and organic solvents (e.g., acetone, ethyl alcohol, acetonitrile, dichloromethane, etc.). Additionally, polypropylene and polystyrene are hydrophobic and provide a low fluorescence background. Amino groups may be introduced onto the polypropylene and polystyrene surface by using a plasma discharge in an ammonia or organic-amine-containing gas, as described in co-pending U.S. patent application Ser. No. 09/694,701, supra. Polypropylene and polystyrene substrates are particularly useful for direct adsorption. Other suitable substrates for purposes of this invention include, but are not limited to, nitrocellulose, nylon, or other polymeric membrane materials, glass, silica, ceramic, gold or other metallic porous and non-porous materials, or a porous foam, such as Porex polypropylene.

Preferably, the substrate is surface-modified prior to contacting with the sample aliquots by introducing a functionality that is capable of producing self-assembling monolayers of the target biopolymer(s) and/or analyte(s) in the sample. Such functionality includes, but is not limited to, functional groups, such as acyl fluoride and other active esters, amino, carboxyl, hydroxyl, epoxide, thiol, alkanethiols, and their reactive derivatives or intermediates and analogs. In one embodiment, the substrate is modified by the introduction of an amine group. Methods for the introduction of amine groups onto a polypropylene surface are described in commonly assigned U.S. Pat. No. 6,013,789, which is specifically incorporated herein by reference. The aminated polypropylene or polystyrene is then utilized for the direct adsorption of a target biopolymer. In examples where the target biopolymer is DNA, the substrate may further be modified to contain hydrophobic and/or hydrophilic regions. For example, reactive organosilanes or organofluorosilanes, e.g., aldehyde or epoxy-terminated organosilanes, may be applied to the amino-modified surface to create hydrophobic regions, while similarly reactive polyglycols may be attached to create hydrophilic surfaces. The surface of the substrate may also be modified by wetting the substrate with an organic modifier, such as ethanol, methanol, isopropanol, 2-butanol, acetic acid, dextran sulfate or polyacrylic acid, prior to the dispensing step in order to precipitate the DNA.

Direct adsorption of biopolymers onto aminated polypropylene and polystyrene substrates is well suited for use in the construction of genosensors and other array-based systems, such as differential gene expression microarrays. A polypropylene substrate with the adsorbed single sample biopolymers of the present invention may also be used as a device for performing a ligand-binding assay or for performing a hybridization assay, according to this invention. Such a device may also be used in an immunoassay.

In order to accommodate a number of different testing techniques including specialized testing equipment, the substrate may be a part of a variety of devices, such as microtiter plates, test tubes, inorganic sheets, dipsticks, etc. Examples of such shapes and forms of the substrates include, but are not limited to, foams, filaments, threads, sheets, films, slides, gels, membranes, beads, plates, and like structures. A substrate may be fabricated in the form of a planar device having discrete isolated areas in the form of wells, troughs, pedestals, hydrophobic or hydrophilic patches, die-cut adhesive reservoirs, or other physical barriers to fluid flow. Examples of such a substrate include, but are not limited to, a microplate, or the like. Because the substrate of the present invention is particularly useful in the preparation of biopolymer microarrays for the evaluation or identification of biological activity, the substrate is preferably in the form of a device having at least one flat planar surface. Examples of such devices with flat surfaces include, but are not limited to, slides, sheets, films, or the like. For example, when the substrate is in a form of a membrane, it can be affixed to glass slides. The particular device is, in and of itself, unimportant, as long as the substrate is securely affixed to the device without affecting the functional behavior of the substrate or any adsorbed biopolymer. The device should also be stable to any materials into which the device is introduced, e.g., clinical samples, etc.

The size of the substrate can vary and depends upon the final use of the immobilized biopolymers. Those skilled in the art will appreciate that arrays of biopolymers immobilized on miniaturized solid supports ("biochips") have been under development recently. These solid supports can be measured in terms of $mm^2$ and can have numerous different immobilized biopolymers, each attached to a different site-specific location on the miniaturized solid support.

The microarray, formed as described above, thus comprises an array of discrete aliquots, wherein each discrete location comprises one or more target biopolymers immobilized to a substrate. In accordance with the present invention, the sample microarray of this invention, prepared as described above, is then contacted with one or more probes under conditions that allow for the detection of a target biopolymer(s). For the purpose of the present invention, a "probe" is a molecule that recognizes and binds to (i.e., has an affinity for) the immobilized target biopolymer forming a complex. The probe includes, but is not limited to, biopolymers, such as nucleic acids, polypeptides, proteins, carbohydrates, and their analogs. A probe-target complex forms when a probe and a target have combined through molecular recognition to form a complex. Interactions between the probe and target include, but are not limited to, hybridization, immune reactions, or any other specific binding reactions, including covalent binding. For example, when the target is a polynucleotide, the probe may comprise a polynucleotide that is substantially complementary to the target polynucleotide. In this embodiment, the probe that is "substantially complementary" is a known sequence of a nucleic acid that is designed to be sufficiently complementary to a sequence of a target nucleic acid, such that the probe and the target nucleic acid strand will hybridize under selected stringency conditions. When the target is a receptor or a ligand, the probe may comprise a ligand or a receptor, respectively, that recognizes and binds to the target receptor or ligand. When the target is an antigen, the probe may comprise an antibody that recognizes the antigen, or vice versa.

The steps of contacting the probes with the sample microarray of immobilized target biopolymer(s) is conducted under conditions that allow the formation of stable complexes between probes and targets. For example, when probe polynucleotides are contacted with target polynucleotides immobilized on a substrate, complementary regions on the target and the probe polynucleotides hybridize with each other, forming probe-target complexes. The selection of such conditions is within the level of skill in the art and include those in which a low, substantially zero, percentage of mismatched hybrids form. The precise conditions depend, however, on the desired selectivity and sensitivity of the assay. Such conditions include, but are not limited to, the hybridization temperature, the ionic strength and viscosity of the buffer, and the respective concentrations of the target and probe biopolymers. Hybridization conditions may be initially chosen to correspond to those known to be suitable in standard procedures for hybridization, and then optimized for use with the particular substrate.

In accordance with embodiments of the present invention, the probes may be labeled with a reporter. As used herein, "reporter" refers to a chemical moiety that provides the ability to detect a target:probe complex. The reporter may be detected by such characteristics as color change, luminescence, fluorescence, or radioactivity. Examples of reporters include, but are not limited to, dyes, chemiluminescent compounds, enzymes, fluorescent compounds, metal complexes, magnetic particles, biotin, haptens, radio frequency transmitters, radioluminescent compounds, radioactive-labeled biomolecules, dye-labeled beads, quantum dots, and bar coded particles. One skilled in the art can readily determine a suitable reporter once the type of probe biopolymer to be utilized is determined.

The labeling procedure may occur prior to analysis (direct labeling) or after complex formation (indirect labeling). Many binding pairs are known in the art for indirect labeling, including, for example, biotin-avidin, biotin-streptavidin, hapten-antihapten antibody, sugar-lectin, and the like. An example of indirect labeling would be the biotinylation of a probe polynucleotide, hybridization with a target, and reaction of the target-probe complexes with a streptavidin-alkaline phosphatase conjugate. The biotin moieties retained after the hybridization with probe polynucleotides bind to a streptavidin-alkaline phosphatase conjugate, which then acts on a chromogenic substrate, such as Enzyme Labeled Fluorescent (ELF) reagent (Molecular Probes, Inc.).

An advantage of the sample microarray of this invention is that it can be probed in multiplex. That is, the sample microarray can be contacted with one probe or with a plurality of known probes to analyze the sample for one or more biopolymers of interest.

In one embodiment, the microarray of this invention is contacted with a single probe. Alternatively, the microarray of this invention is probed in multiplex, that is, the microarray is contacted with a plurality of probes. For example, in one embodiment, each element (aliquot) of the array is contacted with a different probe. That is, the first element of the microarray is contacted with a first known probe, the second element of the microarray is contacted with a second known probe, etc., wherein the first, second, etc. probes may be the same or different. For example, the sample microarray could be contacted with one probe, or with four probes, each having a different, distinguishable label, etc. Since the composition of each probe is known, and since the deposition location of each probe is known, it is not necessary that each probe comprises a different label. Rather, all that is required is that the site at which each probe is deposited be monitored for tracking. Consequently, each probe can be labeled with the same reporter. Alternatively, some or all of the probes can be labeled with different reporters that are distinguishable from one another.

An alternative embodiment for probing the microarray of this invention in multiplex comprises contacting each element of the microarray with a plurality or set of distinguishably labeled probes. The set of probes used to interrogate each site on the microarray need not be the same. Thus, the first element of the array can be contacted with a first set of probes, the second element can be contacted with a second set of probes that is different than the first set, etc. For example, a 1536-plated sample, e.g., an array comprising 1536 discrete, equivalent aliquots of the sample could be interrogated with 1536 probes labeled with the same reporter, or with 6144 probed labeled with four different, distinguishable reporters, or with 24,576 probes labeled with 16 different, distinguishable reporters, etc.

It is also possible to do multiple hybridizations on the same sample microarray to increase the number of probes for analysis. For example, a 1536-plated sample can undergo hybridization with a set of 16 different, distinguishable labeled probes. When the analysis is concluded, the plated sample is stripped of the probes and then addressed with a different set of labeled probes.

The present invention accommodates the simultaneous screening ("multiplexing") of a large number of potential target biopolymers in a single reaction using multiple probes. In practice, the actual number of probe biopolymers that are pooled for simultaneous hybridization is determined according to the diagnostic need. Preferably, the probes are labeled. The various probes can be labeled with the same reporter groups. Alternatively, the reporter groups on the different types of probes can be different.

Accordingly, this invention includes a method for identifying a plurality of target biopolymers in a single sample, comprising:

a) preparing a microarray of the sample by dispensing aliquots of the sample at discrete sites onto a substrate, wherein each of the aliquots contains the same amount of said target biopolymers;

b) immobilizing the target biopolymers onto the substrate;

c) contacting the microarray with a plurality of labeled probes specific for each of the target biopolymers under conditions that allow the formation of a complex between each of the target biopolymers and the labeled probe specific for the target biopolymers; and d) detecting the complexes as a measurement of the presence or the amount of the target biopolymers.

In one embodiment, the sample biopolymer of interest is an oligonucleotide, and the probe is a known oligonucleotide that is complementary to the oligonucleotide of interest. According to the present invention, the probe can be applied at a specific concentration to allow for rapid hybridization, e.g., 30 minutes to one hour, under defined conditions. Such conditions are well known to those skilled in the art and need not be described further.

After an appropriate period of time to allow the complex formation between the target biopolymer and the probe, the microarray is washed to remove uncomplexed probes. The microarray is then scanned to detect bound probes. The signal produced by a bound probe may be detected by a naked eye or by means of a specially designed instrumentation, such as a confocal array reader. For example, in one embodiment, a fluorescent signal is recorded with a charged coupled device (CCD) camera. It will be appreciated by those skilled in the art that the choice of a particular method used to detect and quantify the signal is not crucial for this invention. Essentially, any detection method may be used as long as it provides consistent and accurate results.

It will also be appreciated that this method allows for the rapid and economical screening of a large number of target sequences in a single patient sample. A "sample" refers to a substance that is being assayed for the presence of one or more target biopolymers and/or analytes of interest. In one embodiment, the target biopolymer is a specific nucleic acid sequence, e.g., a portion of a nucleic acid, a particular gene, or a genetic locus in a genomic DNA, known to be involved in a pathological condition or syndrome.

One non-limiting example of the present invention encompasses a method for screening a single sample for target nucleic acid sequences or sequence alterations. For example, the target may be specific DNA sequences in DNA isolated from a patient. In this embodiment, the nucleic acid may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids can include blood, urine, cerebrospinal fluid, semen, tissue exudates, saliva, and fecal materials. Nucleic acids can be extracted from the cell source or body fluid using any of the numerous methods that are standard in the art. It will be understood that the particular method used to extract the nucleic acid will depend on the nature of the source.

Once extracted, the target nucleic acid may be employed in the present invention without further manipulation. Alternatively, one or more specific regions present in the target nucleic acid may be amplified by PCR using methods known to those skilled in the art. In this case, the amplified regions are specified by the choice of particular flanking sequences for use as primers. Amplification at this step provides the advantage of increasing the concentration of specific nucleic acid sequences within the target sequence population.

In practicing one embodiment of the present invention, the untreated or amplified target nucleic acid, bound to a substrate in the form of a microarray, as described above, is incubated with a plurality of biopolymer probes, each comprising a nucleic acid having a sequence that is substantially complementary to a target sequence. The probes may be synthesized chemically by methods that are standard in the art, e.g., using commercially available automated synthesizers. The probes may further comprise a reporter molecule.

The sample array comprising the immobilized target nucleic acid is incubated with the probe biopolymers for a sufficient time and under appropriate conditions to achieve maximal specific hybridization and minimal non-specific, i.e., background and hybridization. The conditions to be considered include the concentration of each biopolymer, the temperature of hybridization, the salt concentration, and the presence or absence of unrelated nucleic acid. The temperature for hybridization can be optimized to be as high as possible for the length of the polymers being used. It will be understood by skilled practitioners that the determination of optimal time, temperature, polymer concentration, and salt concentration should be done in concert.

Following hybridization, unbound probes are removed, if necessary, such as by washing the microarray with a solution containing TMAC or similar compounds, under conditions that preserve perfectly matched nucleic acid:polymer hybrids. Washing conditions, such as temperature, nature, concentration of salts, and time of washing, are determined empirically. At this stage, the presence of bound biopolymer probes may be determined. Different methods for detection will depend upon the label incorporated into the probes.

The invention may be better understood with reference to the accompanying example that is intended for purposes of illustration only and should not be construed as, in any sense, limiting the scope of the present invention, as defined in the claims appended hereto. While the described procedures in the following example are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Example 1

A sample can be dispensed in picoliter volumes with reasonable accuracy. Thus, a single "unknown" sample can be rapidly distributed to thousands of locations in sufficient quantities with precision. For example, the distribution of 1 microliter of sample at 1000 locations requires the delivery of 1 nanoliter (nL) (1000 picoliters) to each site. This is possible with current technology. By comparison, a conventional 1536 microtiter plate would require the use of about 2 milliliters per plate. A typical gene expression experiment on a microscope slide employs 10–15 $\mu$L of sample. Thus, a 15 $\mu$L sample would allow the distribution of about 10 nL to each well (15,000 nL/1500 wells).

Currently, a reasonably sized sample contains 1–2 $\mu$g mRNA (1000–2000 ng). If 15 ng in a 15,000 nL sample is distributed equally over 1500 wells, then 10 nL containing 1 ng is placed in each well (1500 ng/15,000 nL)×10 nL). This amount of nucleic acid can be detected by the use of labeled probes with signal amplification.

Example 2

A Human IgG sample was evenly distributed onto 200 $\mu$L aliquots, each containing approximately 1 femtomole of protein. The protein was covalently attached onto an acyl fluoride-activated polypropylene substrate. The sample was developed using an anti-Human IgG-alkaline phosphatase conjugate. Signal was generated using the ELF reagent. The developed microarray is shown in FIG. 1. In this example, a 3% CV (coefficient of variation) was obtained for the mean signal intensities of the 36 distributed sample aliquots. Thus, the sample was successfully dispensed and subsequently immobilized to the surface into equivalent elements of the microarray.

The invention may be embodied in other specific forms without departing from its essential characteristics. The described embodiments are to be considered in all respects only as illustrative and not as restrictive. Indeed, those skilled in the art can readily envision and produce further embodiments, based on the teachings herein, without undue experimentation. The scope of the invention is, therefore, indicated by the appended claims rather than by the foregoing description. All changes that come within the meaning and range of the equivalence of the claims are to be embraced within their scope.

What is claimed is:

1. A method for detecting a target biopolymer in a sample, comprising:
    (a) preparing a microarray of said sample by dispensing aliquots of said sample at discrete sites onto a substrate and immobilizing said target biopolymer on said substrate, wherein the microarray is an array of dots, each dot having a diameter from about 1 to 500 microns, wherein each of said aliquots contains the same amount of said target biopolymer;
    (b) contacting said microarray with one or a plurality of probe biopolymers under conditions that allow the formation of one or a plurality of complexes, each complex comprising said target biopolymer and one of said probe biopolymers, wherein said probe biopolymers are dispensed on said dots in said microarray; and
    (c) detecting the presence of and quantifying said complexes as a measurement for the presence or the amount of the target biopolymer in said sample.

2. The method of claim 1, wherein the preparation of said microarray further comprises dispensing said sample aliquots on said substrate by a method selected from the group consisting of jet printing, piezoelectric dispensing methods, solenoid dispensing methods, thermal dispensing methods, solid pin contact printing methods, capillary quill contact printing methods, microfluidic-based printing, and silk screening.

3. The method of claim 1, wherein said aliquots comprise picomole amounts of said target biopolymer.

4. The method of claim 1, wherein said aliquots comprise femtomole amounts of said target biopolymer.

5. The method of claim 1, wherein said aliquots comprise attomole amounts of said target biopolymer.

6. The method of claim 1, wherein said aliquots comprise zeptomole amounts of said target biopolymer.

7. The method of claim 1, wherein said target biopolymer or said probe biopolymer is selected from the group consisting of polynucleotides, polypeptides, carbohydrates, and analogs thereof.

8. The method of claim 7, wherein said polynucleotide is selected from the group consisting of amplified DNA, cDNA, single-stranded DNA, double-stranded DNA, peptide nucleic acids (PNA), RNA, and mRNA.

9. The method of claim 7, wherein said polypeptide is selected from the group consisting of antibodies, antibody fragments, antigens, ligands, and receptors.

10. The method of claim 1, wherein said target biopolymer is a first polynucleotide and said probe biopolymer is a second polynucleotide that is complementary to said first polynucleotide.

11. The method of claim 1, wherein said target biopolymer is a receptor and said probe biopolymer is a ligand for said receptor.

12. The method of claim 1, wherein said target biopolymer is an antigen and said probe biopolymer is an antibody specific for said antigen.

13. The method of claim 1, wherein said probe is labeled with a reporter selected from the group consisting of dyes, chemiluminescent compounds, enzymes, fluorescent compounds, metal complexes, magnetic particles, biotin, haptens, radio frequency transmitters, radioluminescent compounds, radioactive-labeled biomolecules, dye-labeled beads, quantum dots, and bar coded particles.

14. The method of claim 1, wherein said substrate is made of crosslinked polymers, porous foam, nitrocellulose, nylon, glass, silica, ceramic, gold, porous metallic materials, non-porous metallic materials, and surface modified materials.

15. The method of claim 14, wherein said crosslinked polymers are selected from the group consisting of polypropylene, polyethylene, polystyrene, and carboxylated polyvinylidene fluoride.

16. The method of claim 14, wherein said surface-modified materials are modified with functional groups selected from the group consisting of acyl fluoride, esters, amino, carboxyl, hydroxyl, epoxide, thiol, and alkanethiols.

17. The method of claim 1, wherein said target biopolymer is immobilized on the substrate by direct adsorption or covalent attachment.

18. The method of claim 1, wherein said support is in the form of foams, filaments, threads, sheets, films, slides, gels, membranes, beads, plates, and planar devices having discrete isolated areas in the form of wells, troughs, pedestals, hydrophobic or hydrophilic patches, die-cut adhesive reservoirs, or other physical barriers to fluid flow.

19. The method of claim 1, wherein the surface of said support is modified to contain hydrophobic and/or hydrophilic regions prior to said dispensing step.

20. The method of claim 1, wherein said substrate is wetted with an organic modifier selected from the group consisting of ethanol, methanol, isopropanol, 2-butanol, acetic acid, dextran sulfate and polyacrylic acid, prior to said dispensing step.

21. The method of claim 1, further comprising co-dispensing an internal standard with said sample to determine the concentration of said target biopolymer in said aliquots.

22. The method of claim 1, wherein in step (b), said microarray is contacted with a plurality of probe biopolymers.

23. The method of claim 22, wherein each aliquot is contacted with a different probe biopolymer.

24. The method of claim 22, wherein said probe biopolymers are labeled with identical reporter groups.

25. The method of claim 22, wherein said probe biopolymers are labeled with reporters that are distinguishable from one another.

26. The method of claim 1, wherein in step (b), each of said aliquots is contacted with a plurality of probe biopolymers.

27. The method of claim 26, wherein said probe biopolymers are labeled with reporters that are distinguishable from one another.

28. The method of claim 1, wherein said aliquots are deposited onto said substrate at about 1 to 1536 sites per square millimeter of the substrate surface area.

29. The method of claim 1, wherein said substrate is a multiple well microplate, and said aliquots are deposited at between 1 to 1536 sites per well of said microplate.

30. A method for detecting a target nucleic acid in a sample, comprising:

(a) preparing a microarray of said sample by dispensing aliquots of said sample at discrete sites onto a substrate and immobilizing said target nucleic acid on said substrate, wherein the microarray is an array of dots, each dot having a diameter from about 1 to 500 microns, wherein each of said aliquots contains the same amount of said target nucleic acid;

(b) contacting said microarray with one or a plurality of labeled nucleic acid probes under hybridizing conditions that allow the formation of one or a plurality of complexes, each complex comprising said target nucleic acid and one of said probes, wherein said probe is a nucleic acid that is substantially complementary to said target nucleic acid, wherein said labeled nucleic acid probes are dispensed on said dots in said microarray; and (c) detecting the presence of and quantifying said complexes as a measurement for the presence or the amount of said target nucleic acid in said sample.

31. The method of claim 30, wherein the preparation of said microarray further comprises dispensing said sample aliquots on said substrate by a method selected from the group consisting of jet printing, piezoelectric dispensing methods, solenoid dispensing methods, thermal dispensing methods, solid pin contact printing methods, capillary quill contact printing methods, microfluidic-based printing, and silk screening.

32. The method of claim 30, wherein said aliquots comprise picomole amounts of said target nucleic acid.

33. The method of claim 30, wherein said aliquots comprise femtomole amounts of said target nucleic acid.

34. The method of claim 30, wherein said aliquots comprise attomole amounts of said target nucleic acid.

35. The method of claim 30, wherein said aliquots comprise zeptomole amounts of said target nucleic acid.

36. The method of claim 30, wherein said target nucleic acid is selected from the group consisting of single-stranded RNA, mRNA, single-stranded DNA, double-stranded DNA, amplified DNA, cDNA and PNA.

37. The method of claim 30, wherein said labeled probe is selected from the group consisting of single-stranded RNA, mRNA, single-stranded DNA, double-stranded DNA, amplified DNA, cDNA, and PNA.

38. The method of claim 30, wherein said probe is labeled with a reporter selected from the group consisting of dyes, chemiluminescent compounds, enzymes, fluorescent compounds, metal complexes, magnetic particles, biotin, haptens, radio frequency transmitters, radioluminescent compounds, radioactive-labeled biomolecules, dye-labeled beads, quantum dots, and bar coded particles.

39. The method of claim 30, wherein said substrate is made of crosslinked polymers, porous foam, nitrocellulose, nylon, glass, silica, ceramic, gold, porous metallic materials, non-porous metallic materials, and surface-modified materials.

40. The method of claim 39, wherein said crosslinked polymers are selected from the group consisting of polypropylene, polyethylene, polystyrene, and carboxylated polyvinylidene fluoride.

41. The method of claim 39, wherein said surface-modified materials are modified with functional groups selected from the group consisting of acyl fluoride, esters, amino, carboxyl, hydroxyl, epoxide, thiol, and alkanethiols.

42. The method of claim 30, wherein said substrate is wetted with an organic modifier selected from the group consisting of ethanol, methanol, isopropanol, 2-butanol, acetic acid, dextran sulfate and polyacrylic acid, prior to said dispensing step.

43. The method of claim 30, further comprising co-dispensing an internal standard with said sample to determine the concentration of said target nucleic acid in said aliquots.

44. The method of claim 30, wherein in step (b), the microarray is contacted with a plurality of probes.

45. The method of claim 44, wherein each aliquot is contacted with a different probe.

46. The method of claim 44, wherein each probe is labeled with an identical reporter.

47. The method of claim 44, wherein said probes are labeled with reporters which are distinguishable from one another.

48. The method of claim 30, wherein each of said aliquots is contacted with a plurality of probes.

49. The method of claim 48, wherein said probes are labeled with reporters which are distinguishable from one another.

50. The method of claim 30, wherein said aliquots are deposited onto said substrate at about 1 to 1536 sites per square millimeter of the substrate surface area.

51. The method of claim 30, wherein said substrate is a multiple well microplate, and said aliquots are deposited at between 1 to 1536 sites per well of said microplate.

52. A method for identifying one or more target analytes in a sample, comprising:

(a) preparing a microarray of said sample by dispensing aliquots of said sample at discrete sites onto a substrate and immobilizing said analytes on said substrate, wherein the microarray is an array of dots, each dot having a diameter from about 1 to 500 microns, wherein each of said aliquots contains the same amount of said target analytes;

(b) contacting said microarray with a plurality of labeled probes specific for each of said target analytes under conditions that allow formation of a plurality of complexes, each complex comprising one of said target analytes and one of said labeled probes specific for said target analyte, wherein said plurality of labeled probes are dispensed on said dots in said microarray; and (c) detecting and quantifying said complexes as a measurement of the presence or the amount of said target analytes.

53. The method of claim 52, wherein the preparation of said microarray further comprises dispensing said sample aliquots on said substrate by a method selected from the group consisting of jet printing, piezoelectric dispensing methods, solenoid dispensing methods, thermal dispensing methods, solid pin contact printing methods, capillary quill contact printing methods, microfluidic-based printing, and silk screening.

54. The method of claim 52, wherein said analyte is selected from the group consisting of biopolymers, drugs, small organic molecules, nucleic acids, proteins, receptors, antigens, carbohydrates, cells, cellular fragments, and tissues.

55. The method of claim 52, wherein said probe is selected from the group consisting of nucleic acids, antibodies, antibody fragments, ligands, and carbohydrates.

56. The method of claim 52, wherein said label is selected from the group consisting of dyes, chemiluminescent compounds, enzymes, fluorescent compounds, metal complexes, magnetic particles, biotin, haptens, radio frequency transmitters, radioluminescent compounds, radioactive-labeled biomolecules, dye-labeled beads, quantum dots, and bar coded particles.

57. The method of claim 52, wherein said aliquots comprise picomole amounts of said analyte.

58. The method of claim 52, wherein said aliquots comprise femtomole amounts of said analyte.

59. The method of claim 52, wherein said aliquots comprise attomole amounts of said analyte.

60. The method of claim 52, wherein said aliquots comprise zeptomole amounts of said analyte.

61. The method of claim 52, wherein said substrate is made of crosslinked polymers, porous foam, nitrocellulose, nylon, glass, silica, ceramic, gold, porous metallic materials, non-porous metallic materials, and surface-modified materials.

62. The method of claim 52, wherein said surface-modified materials are modified with functional groups selected from the group consisting of acyl fluoride, esters, amino, carboxyl, hydroxyl, epoxide, thiol, and alkanethiols.

63. The method of claim 52, wherein the surface of said support is modified to contain hydrophobic and/or hydrophilic regions prior to said dispensing step.

64. The method of claim, 52, wherein said substrate wetted with an organic modifier selected from the group consisting of ethanol, methanol, isopropanol, 2-butanol, acetic acid, dextran sulfate and polyacrylic acid, prior to said dispensing step.

65. The method of claim 52, further comprising co-dispensing an internal standard with said sample to determine the concentration of said analytes in said aliquots.

66. The method of claim 52, wherein each aliquot is contacted with a different probe.

67. The method of claim 66, wherein each probe is labeled with an identical reporter.

68. The method of claim 66, wherein each probe is labeled with a different reporter.

69. The method of claim 52, wherein each aliquot is contacted with a plurality of probes.

70. The method of claim 52, wherein said aliquots are deposited onto said substrate at about 1 to 1536 sites per square millimeter of the substrate surface area.

71. The method of claim 52, wherein said substrate is a multiple well microplate, and said aliquots are deposited at between 1 to 1536 sites per well of said microplate.

* * * * *